(12) United States Patent
Woldesus et al.

(10) Patent No.: US 10,078,040 B2
(45) Date of Patent: Sep. 18, 2018

(54) WIRE FLEXIBILITY TESTING APPARATUS

(71) Applicant: Champlain Cable Corporation, Colchester, VT (US)

(72) Inventors: Futsum G. Woldesus, Essex Junction, VT (US); Douglas Mark Cutler, Milton, VT (US)

(73) Assignee: CHAMPLAIN CABLE CORP., Colchester, VT (US)

( * ) Notice: Subject to any disclaimer, the term of this patent is extended or adjusted under 35 U.S.C. 154(b) by 0 days.

(21) Appl. No.: 15/214,698

(22) Filed: Jul. 20, 2016

(65) Prior Publication Data

US 2018/0024033 A1   Jan. 25, 2018

(51) Int. Cl.
*G01N 3/08* (2006.01)
*G01N 3/20* (2006.01)
*G01N 3/22* (2006.01)

(52) U.S. Cl.
CPC .......... *G01N 3/08* (2013.01); *G01N 3/20* (2013.01); *G01N 3/22* (2013.01)

(58) Field of Classification Search
CPC .......... G01N 3/08; G01N 3/20; G01N 3/22
USPC .......................................................... 73/794
See application file for complete search history.

(56) References Cited

U.S. PATENT DOCUMENTS

| | | | | |
|---|---|---|---|---|
| 1,400,137 | A | * 12/1921 | Bines | ............... B29C 47/0009 264/148 |
| 2,099,955 | A | * 11/1937 | Edwards | ............ E21B 47/0006 346/150.1 |
| 2,756,590 | A | * 7/1956 | Gehman | ................... G01N 3/06 33/788 |
| 4,403,499 | A | * 9/1983 | Sack | ....................... G01N 3/32 73/158 |
| 5,549,542 | A | 8/1996 | Kovalcheck | |
| 5,676,653 | A | 10/1997 | Taylor et al. | |
| 5,994,910 | A | 11/1999 | Downes, Jr. et al. | |
| 6,096,004 | A | 8/2000 | Meglan et al. | |
| 7,096,743 | B2 | * 8/2006 | Vogel | ....................... B07C 1/16 73/159 |
| 7,371,210 | B2 | 5/2008 | Brock et al. | |

* cited by examiner

*Primary Examiner* — Harshad R Patel
*Assistant Examiner* — Jamel Williams
(74) *Attorney, Agent, or Firm* — Mark Levy

(57) ABSTRACT

A flexibility testing apparatus for wire or cable. Two circular, rotatable gears are mounted to a frame, one gear being a drive gear and the other being a driven gear. The driven gear is coplanar with the drive gear and the drive gear teeth are enmeshed with the driven gear teeth. Two rods are connected to the mounting holes of the drive gear and the wire or cable is attached to the rods using barrel end clamps for flexing. The driven gear can be rotated at different speeds by an electric motor or a pneumatic driving device.

7 Claims, 6 Drawing Sheets

WIRE FLEXIBILITY TESTING APPARATUS

FIELD OF THE INVENTION

This invention relates to testing apparatus and, more particularly, to an apparatus for testing the flexibility of wire or cable.

BACKGROUND OF THE INVENTION

Electrical wires and cables have a great number of uses. They are used to transmit power, both high voltage and low voltage, over great distances and within the confines of small electrical devices. They are used to form electrical components, including motors, transformers, dynamos and generators. Single wires can be formed of uninsulated, conductive metal, such as copper, silver, gold, platinum, tin, or lead, or more sophisticated compositions such as metal alloys, copper clad aluminum, etc.

The wires can also be insulated with rubber material, such as natural rubber, thermoplastic rubber, neoprene (polychloroprene), styrene butadiene rubber, silicone, fiberglass, ethylene propylene rubber, chlorosulfonated polyethylene, and ethylene propylene diene monomer; plastics, such as polyvinyl chloride (PVC), semi-rigid PVC, plenum polyvinyl chloride (plenum PVC), polyethylene, polypropylene, polyurethane, chlorinated polyethylene, and nylon; and fluoropolymers, such as PFA, polytetrafluoroethylene, fluorinated ethylene propylene, ETFE Tefzel and ECTFE Halar, polyvinylidene fluoride, and thermoplastic elastomers. Insulated wires can be bundled into coaxial cables.

Wires and cables are expected to retain their electrical and physical characteristics regardless of environmental conditions (i.e., in many atmospheric settings, under water or other liquids, under pressure, within great temperature ranges, etc.). Moreover, although certain wires and cables are expected to be stationary during the course of their useful life, certain wires and cables are intended to be twisted, bent or otherwise moved. It is important, therefore, for a wire or cable manufacturer to know in advance whether its product is suitable for such dynamic situations.

Testing the flexibility of wire and cable under adverse conditions (e.g., subzero and continuous bending applications) can be both advantageous and essential.

DESCRIPTION OF RELATED ART

U.S. Pat. No. 5,994,910 issued to Downes, Jr., et al. on Nov. 30, 1999 for APPARATUS, AND CORRESPONDING METHOD, FOR STRESS TESTING WIRE BOND-TYPE SEMI-CONDUCTOR CHIPS discloses an apparatus and corresponding method for stress-testing wire bond-type semiconductor chips. The apparatus includes a clamp housing, with a spring-loaded screw extending through the top end of the housing. Contained within the clamp housing is a substantially rigid, electrically insulating base plate positioned at a lower end of the clamp housing. The upper surface of the base plate includes a depression which contains an insert.

U.S. Pat. No. 5,549,542 issued to Kovalcheck on Aug. 27, 1996 for DEFLECTABLE ENDOSCOPE discloses a minimally intrusive endoscope having a deflectable tip. A remotely bendable section adjacent a distal viewing tip enables movement of the tip between a neutral position and angularly disposed positions. A deflection control lever on a proximal control member causes deflection of the viewing tip by means of two sets of operating cables which are operatively connected at one end to the control member and at the other end to axially spaced locations along the controllably bendable section.

U.S. Pat. No. 5,676,653 issued to Taylor, et al. on Oct. 14, 1997 for KINK-RESISTANT STEERABLE CATHETER ASSEMBLY discloses a kink-resistant steerable catheter assembly suitable for microwave ablation that includes a handle, a catheter and a steering control. The catheter has a flexible, torque-transmitting and axially incompressible proximal or body portion terminating in a proximal end attached to the handle, and a flexible and axially compressible distal or tip portion terminating in a distal end. The control is disposed in and actuatable from the handle, for placing tension on one of a pair of steering wires while relaxing tension on the other of the pair of steering wires, thereby to bend the distal end of the coaxial cable extension toward the tensed one of the steering wires.

U.S. Pat. No. 6,096,004 issued to Meglan, et al. on Nov. 30, 1999 for MASTER/SLAVE SYSTEM FOR THE MANIPULATION OF TUBULAR MEDICAL TOOLS discloses a master/slave system used for performing a surgical procedure. The system employs a master actuator with cylindrical controls and a slave actuator that engages the tools. The master actuator and slave actuator are electrically coupled to electrical interface circuitry by drive signals and sense signals. The master and slave actuators contain sensors that sense translation and rotation of the controls and tools with respect to their longitudinal axes, and provide sense signals indicative of these motions to the interface circuitry. The master and slave actuators also contain motors respectively engaging the controls and tools to cause translational and rotational movement of these components in response to the drive signals generated by the interface circuitry.

U.S. Pat. No. 7,371,210 issued to Brock, et al. on May 13, 2008 for FLEXIBLE INSTRUMENT discloses a remote control flexible instrument system, employing a shaft which supports a tool, which has proximal and distal ends with at least a portion thereof extending through a lumen of the human body. A master station including an input device provides control of the instrument situated at a slave station. The master station can control at least one degree-of-freedom of the flexible instrument. A controller intercouples the master and slave stations and is operated in accordance with a computer algorithm that receives a command from the input device for controlling at least one degree-of-freedom of the catheter so as to respond in accordance with action at the input device. The flexible instrument further comprises a controlled flexible segment along the shaft, for controlled bending at the flexible segment to guide the shaft and to dispose the tool at an operative site.

SUMMARY OF THE INVENTION

In accordance with the present invention, there is provided a flexibility testing apparatus for wire or cable. Two circular, rotatable gears are mounted to a frame, one gear being a drive gear and the other being a driven gear. The driven gear is coplanar with the drive gear and the drive gear teeth are enmeshed with the driven gear teeth. A mounting hole is spaced apart from the center of each of the gears. Two rods are connected to the mounting holes of the drive gear and the wire or cable is attached to the rods using barrel end clamps for flexing. The driven gear can be rotated at different speeds by an electric motor or a pneumatic driving device.

It is therefore an object of the invention to provide an apparatus to test flexibility of wire and cable under adverse conditions.

It is a further object of the present invention to provide a flexibility testing apparatus that induces stress on such wire and cable by repetitive bending.

It is a further object of the present invention to provide a flexibility testing apparatus that bends wire and cable repetitively.

These and other objects and advantages of the present invention are more readily apparent with reference to the following detailed description and the accompanying drawings.

BRIEF DESCRIPTION OF THE DRAWINGS

A complete understanding of the present invention may be obtained by reference to the accompanying drawings, when considered in conjunction with the subsequent detailed description, in which.

Like reference numerals refer to like parts throughout the several views of the drawings.

DETAILED DESCRIPTION OF THE PREFERRED EMBODIMENT

Although the following detailed description contains specific details for the purposes of illustration, those of ordinary skill in the art will appreciate that variations and alterations to the following details are within the scope of the invention. Accordingly, the exemplary embodiments of the invention described below are set forth without any loss of generality to, and without imposing limitations upon, the claimed invention.

Figure 1:
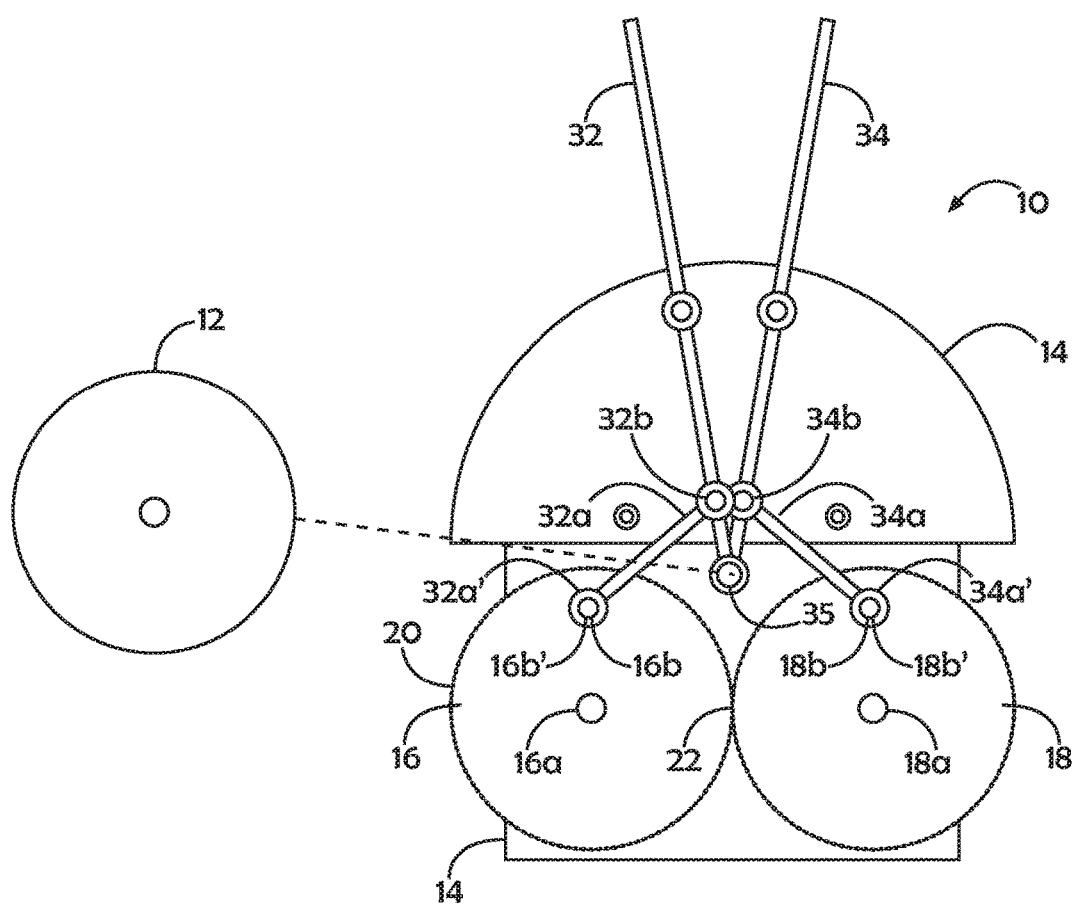
FIG. 1 is a front view of the flexibility testing apparatus with the cover removed in accordance with the invention.
Figure 2:
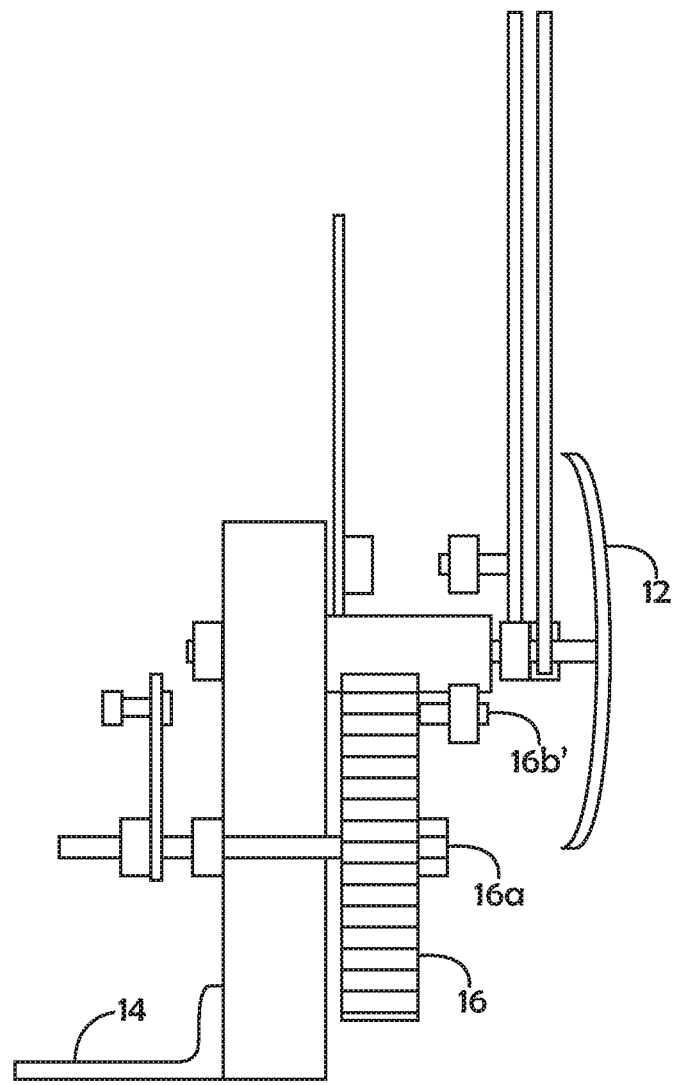
FIG. 2 is a side view of the flexibility testing apparatus shown in FIG. 1.

Referring now to FIGS. 1 and 2, there are shown a front and side view, respectively, of the flexibility testing apparatus 10 in accordance with the invention. A cover 12 is removed from the apparatus 10 in FIG. 1 to show the components thereof in greater detail.

A planar frame 14 is provided. A drive gear 16 and a driven gear 18 are rotatively mounted to the frame 14 by shafts 16a and 18a, respectively, at the center of gears 16 and 18. The gears 16 and 18 are coplanar. Both gears 16, 18 are adapted to move clockwise and counterclockwise, as described hereinbelow. Both drive gear 16 and driven gear 18 have identical dimensions and identical number of gear teeth 20 at the peripheries thereof. Gear teeth 20 of both gears 16, 18 enmesh at position 22.

Each gear 16, 18 has a mounting hole 16b, 18b spaced apart from their respective shafts 16a, 18a. The distance between mounting holes 16b, 18b and the gear shafts 16a, 16b, respectively, can change with various embodiments of the invention. In fact, more than one spaced apart mounting holes 16b, 18b can be provided on respective gears 16, 18, each being a different distance from the gear shafts 16a, 18a, as desired. The mounting holes 16b, 18b have respective shafts 16b', 18b' protruding therefrom perpendicular to the plane of the gears 16, 18.

Slipping over the mounting hole shafts 16b', 18b' are push/pull connecting rod links 32a, 34a, respectively, each connecting rod link 32a, 34a being terminated at both extremities in ball-type ends 32a', 34a'. The opposite end of each rod link 32a, 34a is slipped over an actuation lever shaft 32b, 34b, respectively, connected to actuation levers 32, 34. The distal ends of actuation levers 32, 34 are pivotally mounted to a pivot shaft 35 mounted to frame 14.

Connected to drive gear shaft 16a is a mechanism, not shown, for rotating the shaft 16a and thence the drive gear 16. The mechanism can be a suitable electric motor or a pneumatic driving device.

Figure 6:
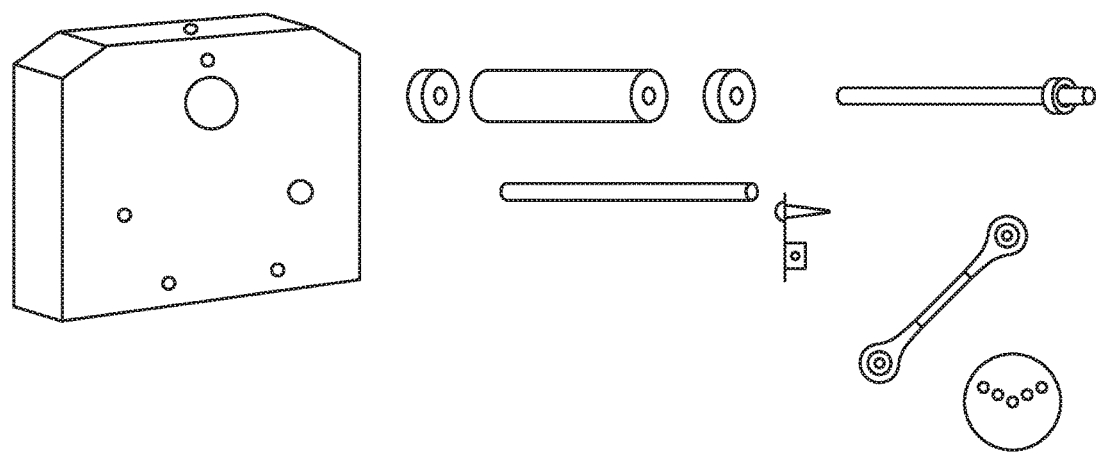
FIG. 6 is a rear, exploded view of components in the flexibility testing apparatus.

FIG. 6 is a rear, exploded view of components in the flexibility testing apparatus.

Figure 3:
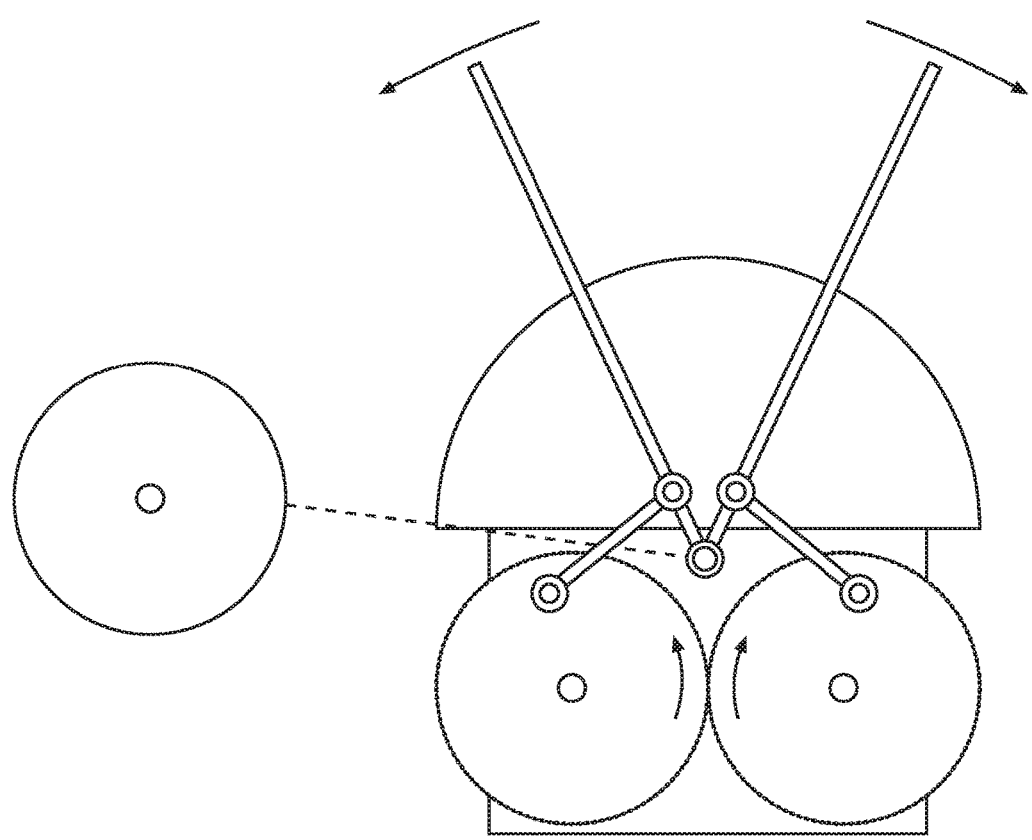
FIG. 3 is a front view of the flexibility testing apparatus shown in FIGS. 1 and 2, illustrating the directions of gear motion.
Figure 5:
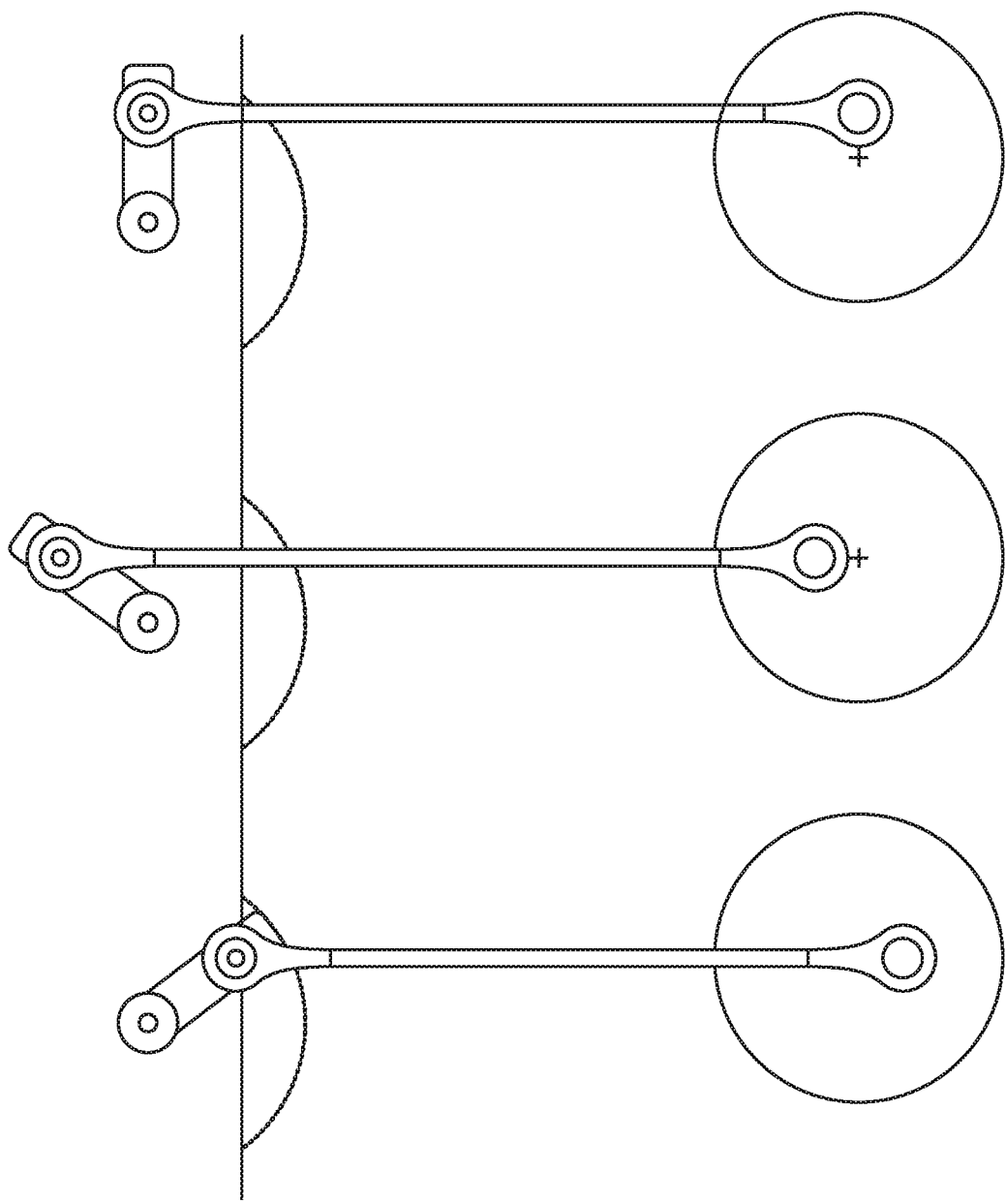
FIG. 5 is a partial rear view of the drive gear and successive motion of the reciprocation wheel.

Referring now also to FIG. 3, there is shown a front view of the flexibility testing apparatus 10, illustrating the directions of gear motion operation. In operation, as drive gear 16 is driven in a counterclockwise direction, driven gear 18 is forced to move clockwise. Push/pull connecting rod links 32a, 34a move apart, separating actuation levers 32, 34 in a "bird wing flap" movement. A more detailed illustration of the push/pull connecting rod links 32a, 34a is shown in FIG. 5. A wire or cable under test 40 is connected to actuation levers 32, 34 via barrel end clamps 32c, 34c, respectively, to stretch or bend wire 40.

Figure 4:
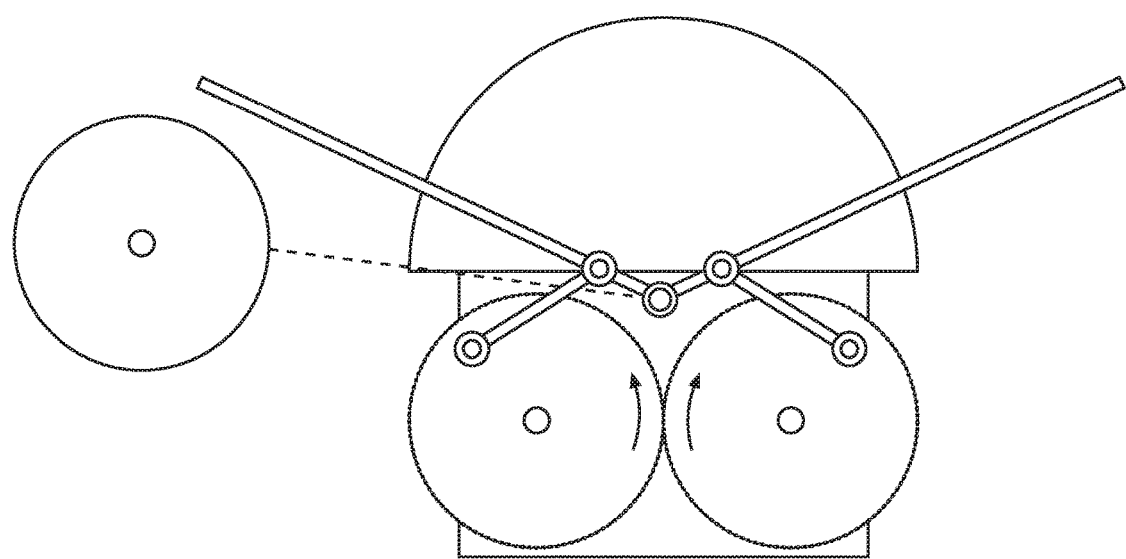
FIG. 4 is a front view of the flexibility testing apparatus shown in FIGS. 1 and 2, illustrating progressive gear motion.

As drive gear 16 continues to make a revolution, as shown in FIG. 4, push/pull connecting rod links 32a, 34a move together, bringing actuation levers 32, 34 together. The wire or cable 40 is thus bent or straightened. The stretching or bending/unbending cycle of wire 40 continues until the insulation/dielectric (not shown) thereof cracks.

The flexibility testing apparatus 10 can vary in size per application and push/pull connecting rod links 32a, 34a can be variable in length. Moreover, the speed of the motor or pneumatic driving device can be adjusted to accommodate different test requirements.

Since other modifications and changes varied to fit particular operating requirements and environments will be apparent to those skilled in the art, the invention is not considered limited to the example chosen for purposes of disclosure and covers all changes and modifications which do not constitute departures from the true spirit and scope of this invention.

Having thus described the invention, what is desired to be protected by Letters Patent is presented in the subsequently appended claims.

What is claimed is:

1. A flexibility testing apparatus for wire or cable comprising:
    a) a planar frame having a front major surface and a rear major surface;
    b) a circular, rotatable drive gear mounted to said frame and proximate said front major surface thereof, said drive gear having a first predetermined diameter and a first predetermined number of teeth disposed along a circumference thereof and a mounting hole spaced apart from a center thereof;
    c) a circular, rotatable driven gear mounted to said frame and proximate said front major surface thereof, said driven gear having a second predetermined diameter and a second predetermined number of teeth disposed along a circumference thereof and a mounting hole spaced apart from a center thereof, said driven gear being coplanar with said drive gear and said drive gear teeth being enmeshed with said driven gear teeth;

d) a drive shaft connected to said center of said drive gear;

e) means operatively connected to said drive shaft for initiating rotation thereof; and f) a moving/bending rod operatively connected to said mounting hole of each gear, said moving/bending rods each having means for mounting one end of a wire or cable thereto.

2. The flexibility testing apparatus in accordance with claim 1, wherein said moving/bending rod of said drive gear and said driven gear comprises:

g) a first connecting rod link connected to a first moving/bending rod and said drive gear mounting hole; and h) a second connecting rod link connected to a second moving/bending rod and said driven gear mounting hole.

3. The flexibility testing apparatus in accordance with claim 1, wherein said connection rod links comprise a ball-type end at each extremity thereof.

4. The flexibility testing apparatus in accordance with claim 1, wherein said means for rotating said drive shaft is chosen from the group consisting of: an electric motor and a pneumatic driving device.

5. The flexibility testing apparatus in accordance with claim 4, wherein said means for rotating said drive shaft rotates said drive shaft at a variable speed.

6. The flexibility testing apparatus in accordance with claim 1, wherein said flexibility testing apparatus performs at least one function on said wire or cable chosen from the group consisting of: stretching, compressing, twisting, bending, unbending, and straightening.

7. The flexibility testing apparatus in accordance with claim 1, wherein said second predetermined diameter is equal to said first predetermined diameter and said second predetermined number of teeth is equal to said first predetermined number of teeth.

* * * * *